United States Patent [19]

Ekwall et al.

[11] Patent Number: 5,578,067
[45] Date of Patent: Nov. 26, 1996

[54] MEDICAL ELECTRODE SYSTEM HAVING A SLEEVE BODY AND CONTROL ELEMENT THEREFOR FOR SELECTIVELY POSITIONING AN EXPOSED CONDUCTOR AREA

[75] Inventors: Christer Ekwall, Spånga; Kurt Högnelid, Västerhaninge, both of Sweden

[73] Assignee: Pacesetter AB, Solna, Sweden

[21] Appl. No.: 416,221

[22] Filed: Apr. 4, 1995

[30] Foreign Application Priority Data

Apr. 14, 1994 [SE] Sweden ................................. 9401267

[51] Int. Cl.⁶ ....................................... A61N 1/05
[52] U.S. Cl. ........................ 607/122; 607/123; 607/126; 128/642
[58] Field of Search ............... 607/2, 4, 5, 116, 607/119, 121, 122–128; 606/47; 128/642

[56] References Cited

U.S. PATENT DOCUMENTS

| | | |
|---|---|---|
| 4,010,755 | 3/1977 | Preston . |
| 4,013,081 | 3/1977 | Kolenik . |
| 4,444,195 | 4/1984 | Gold . |
| 4,735,205 | 4/1988 | Chachques et al. .................. 607/2 |
| 4,800,898 | 1/1989 | Hess et al. ........................... 607/122 X |
| 5,044,375 | 9/1991 | Bach, Jr. et al. . |
| 5,056,532 | 10/1991 | Hull et al. ............................ 607/124 |
| 5,172,694 | 12/1992 | Flamming et al. . |
| 5,263,977 | 11/1993 | Adams et al. ....................... 607/122 |

Primary Examiner—William E. Kamm
Assistant Examiner—Jeffrey R. Jastrzab
Attorney, Agent, or Firm—Hill, Steadman & Simpson

[57] ABSTRACT

An electrode apparatus, such as an intravascular or intracardiac pacemaker or defibrillation electrode with an electrode cable has a jacket of insulation enclosing a first elongated, flexible conductor, connected to a first electrode arranged on the electrode cable, and also enclosing at least a second conductor, connected to a conductive surface forming a second electrode arranged on the electrode cable at a distance from the first electrode. In order to achieve an electrode apparatus with which the distance between the electrode on the electrode cable cart be changed in a very simple manner and in which the surface area exposed to tissue of at least one electrode can be enlarged, reduced and even rotated around the electrode cable in certain instances, the electrode apparatus is equipped with at least one sleeve-like body, insulated against the surroundings and slidable on the electrode cable, which at least partially covers the conductive surface and with which the second electrode can be formed whose position in relation to the first electrode and/or whose size can be varied.

36 Claims, 3 Drawing Sheets

MEDICAL ELECTRODE SYSTEM HAVING A SLEEVE BODY AND CONTROL ELEMENT THEREFOR FOR SELECTIVELY POSITIONING AN EXPOSED CONDUCTOR AREA

BACKGROUND OF THE INVENTION

1. Field of the Invention

The present invention relates to an electrode apparatus, such as an intravascular or intracardiac pacemaker or defibrillation electrode of the type having an electrode cable with a jacket of insulation enclosing a first elongated, flexible conductor, connected to a electrode arranged on the electrode cable, and at least a second conductor, connected to a conductive surface arranged on the electrode cable at a distance from the electrode.

2. Description of the Prior Art

Using a bipolar pacemaker electrode apparatus, a heart can be stimulated and cardiac activity sensed with the electrodes arranged on the electrode apparatus. In order to achieve good sensing of cardiac activity, the electrode for this purpose is generally placed at a distance from the stimulation electrode which, in most instances, is arranged at the distal end of the electrode cable. With an implanted intracardiac pacemaker electrode, the stimulation electrode usually presses against the heart wall in the inferior part of the ventricle. If the physician wishes to apply the sensing electrode in the ventricle, atrium or superior vena cava, he or she must select at each implantation occasion, an electrode apparatus for which the distance between the stimulation electrode and the second electrode is such that the latter electrode can be applied at the desired site. Since the size and shape of the heart varies from one patient to another, the physician must have access to a large number of pacemaker electrode apparatuses with different distances between the said electrodes so he or she can select an electrode apparatus in which the distance between the electrodes permits optimal siting of the second electrode. Even with a pacemaker electrode apparatus for intravascular siting, the physician needs to select an electrode cable with an interelectrode distance suitable for the patient in order to achieve optimum sensing and stimulation of the heart.

In U.S. Pat. No. 5,172,694, pacemaker electrode apparatus for intracardiac siting of the type described above is disclosed. By providing the cable of the electrode apparatus with a number of relatively closely spaced consecutive indifferent electrodes, separated from the stimulation electrode, each with its own separate conductor, an attempt was made to reduce the number of electrode apparatuses which have to be stocked at a hospital. When the physician tests these electrodes, individually or in pairs, after the electrode apparatus has been implanted, he or she is able to identify the electrode or electrodes with the best position in the heart or vein and then disconnect the others. The disadvantage of this electrode apparatus is that only a limited number of indifferent electrodes can be arranged on the electrode cable, since the relatively small diameter cable must enclose a corresponding number of conductors. Thus, the portion of the cable length which can be covered with these electrodes is limited, since otherwise the cable's dimensions, flexibility and connections would be adversely affected. Since this length portion is limited, the selectivity available to the physician is correspondingly limited.

U.S. Pat. No. 5,044,375 discloses a defibrillation electrode apparatus for intravascular placement of the aforementioned type. This defibrillation electrode apparatus contains two separately arranged defibrillation electrodes, in addition to a pacemaker stimulation electrode arranged at the distal end of the electrode cable, and a tightly spaced sensing electrode. With this electrode apparatus, the physician is unable to change the distance between the defibrillation electrodes.

SUMMARY OF THE INVENTION

An object of the present invention is to provide an electrode apparatus of the general type initially described, but with which the distance between the electrodes on the electrode cable can be changed with great simplicity and with which the area exposed to tissue of at least one electrode can be enlarged or reduced and, in certain embodiments, rotated around the electrode cable.

This object is achieved in an electrode apparatus constructed in accordance with the principles of the present invention having at least one sleeve-like body, insulated against the surroundings and slidable on the electrode cable, which at least partly covers a conductive surface of the cable and with which a second electrode can be formed whose position in relation to the first electrode and/or whose size can be varied. With this structure for the electrode apparatus, by sliding the sleeve-like body or sleeve-like bodies along the exterior of the cable, the position of the second electrode can be selectively displaced along the conductive surface in relation to the first electrode so that the distance between the electrodes can be changed.

A pacemaker electrode apparatus according to the invention is used preferably in conjunction with "DDD" and "VDD" applications. "DDD" means that both the first and the second electrode are used for detection and stimulation, and "VDD" means that at least one electrode in the atrium senses atrial activity and synchronizes ventricular activity. In both these applications, one electrode is placed in the ventricle and the other in the atrium. Stimulation of the ventricle is inhibited when spontaneous activity is sensed, thus the electrode placed therein performs both sensing and stimulating functions. One or a number of electrodes placed in the atrium is/are often used for bipolar sensing of cardiac activity. The ability to move this bipolar electrode, or these electrodes, along the electrode cable to an optimum position would therefore be highly advantageous.

The pacemaker electrode apparatus is also useful for use in the ventricle, i.e. when both electrodes are in the ventricle and the physician wishes to ascertain the propagation direction of EL ventricular complex. The spontaneous complex starts from the wall of the septum, one-third of the way up from the cardiac apex. A different propagation direction is achieved when stimulation is with a stimulation electrode located at the apex. Knowledge of this can be used for distinguishing spontaneous heart contractions from stimulated contractions, using an electrode apparatus according to the invention whose electrode, not placed at the apex, can be moved to an optimum position in the ventricle.

In one embodiment of the invention, the second electrode is formed from the part of the conductive surface which is not covered by the sleeve-like body. The sleeve-like body is a solid-walled tube (i.e., it has no openings in its tube wall) having opposite ends, and the tube is positioned on the cable so that a portion of the conductive surface extends beyond one of the ends and thereby forms the second electrode. When the body is moved in relation to the conductive surface, the surface area of the second electrode can be enlarged or reduced. In this way, the physician can also change the distance between electrodes by exposing the end of the conductive surface, facing away from the first electrode, or by exposing the opposing end of the conductive surface, facing toward the first electrode.

In a further advantageous embodiment of the invention, the sleeve-like body has at least one opening in its tube wall which is smaller than the size of the conductive surface, whereby the opening can be rotated around and/or slid along the conductive surface by moving or rotating the body. With a body devised in this way, the conductive surface exposed through the opening and forming the electrode can be "aimed" in a desired direction by rotating the body around the longitudinal axis of the cable. In this way, the electrode can achieve a favorable distribution of current in heart tissue both with a pacemaker and a defibrillation apparatus. The opening with a pacemaker electrode apparatus is preferably aimed at excitable tissue. If the sleeve-like body is equipped with fixing means, e.g. in the form of tines, near the electrode formed by the body, the ability to rotate the body so the fixing means are aimed at and affixed to heart wall will be highly advantageous. This rotation will also be advantageous when a defibrillation electrode apparatus is in contact with sensitive venous or heart tissue. With this placement, the body can be rotated so as to serve as insulation against the sensitive tissue.

According to the invention, the conductive surface is formed by a thin coating deposited on the cable jacket insulation. This coating can be e.g. vapor-deposited so the flexibility of the electrode cable is not impaired. According to the invention, the conductive surface can alternatively be formed from part of the second conductor which is stripped of the insulation jacket. The conductive surface can extend over a long portion of the electrode cable. It is only necessary that the sleeve-like body to cover this conductive surface, at least in part.

According to the invention, the conductive surface can alternatively be formed by at least two preferably ring-shaped sub-surfaces connected to a common conductor.

The electrode apparatus can also be advantageously equipped with two sleeve-like bodies which can slide in relation to each other and/or rotate in relation to each other. The conductive surface, which is delineated by the facing, respective opposing ends of the sleeves, can be enlarged or reduced with the sleeve-like bodies. Each sleeve-like body can also be provided with an opening which can be aimed in different directions when the body is rotated around the cable by the physician.

In a preferred embodiment of the invention, the interior wall of at least one of the sleeve-like bodies is provided at least in part with a conductive coating, connected to an electrode arranged on the body, which forms the second electrode. This second electrode can be ring-shaped, semi-ring shaped or have some other advantageous shape. The electrode can be arranged anywhere on the body e.g. at one end of the body. In a defibrillation electrode apparatus, the electrode can also cover a large part of, or the entire body.

In another preferred embodiment of the invention, the electrode apparatus is equipped with a third conductor, running inside the jacket of insulation and connected to a second conductive surface arranged on the electrode cable. The first and the second conductive surfaces are subdivided into sub-surfaces separately spaced along the electrode cable. This electrode apparatus construction is for, e.g., a multipolar pacemaker electrode apparatus.

In another version of the embodiment wherein the electrode apparatus is equipped with sub-surfaces, the sleeve-like body can be provided with two openings, spaced at a distance corresponding to the distance between two sub-surfaces, with the length of one opening being less than the distance between these sub-surfaces. The length of the opening ensures that no opening is able to expose two sub-surfaces simultaneously. When the body is slid along the cable in such a way that each opening exposes one conductive surface, the surfaces being electrically separated from each other, displacement of these electrodes and, accordingly, a change in the distance between them and the first electrode, are achieved in the case of a multipolar pacemaker electrode apparatus.

According to another embodiment of the invention, the length of the sleeve-like body is such that the body's proximal end is accessible to the physician after the first electrode has been applied. In this embodiment, the physician is able to control the body even after implantation and thereby work his or her way to the best position(s) for the second electrode, or second electrodes.

According to the invention, the proximal end of the body can even be equipped with control means with which the body can be slid along or rotated around the electrode cable. The body can therefore be relatively short but still controllable after the electrode apparatus has been implanted.

The interior walls of the sleeve-like bodies and/or the surface of the electrode cable on which the bodies slide can be provided with a coating of lubricant. This facilitates sliding and rotation of the body on the cable.

DESCRIPTION OF THE PREFERRED EMBODIMENTS

Figure 1:
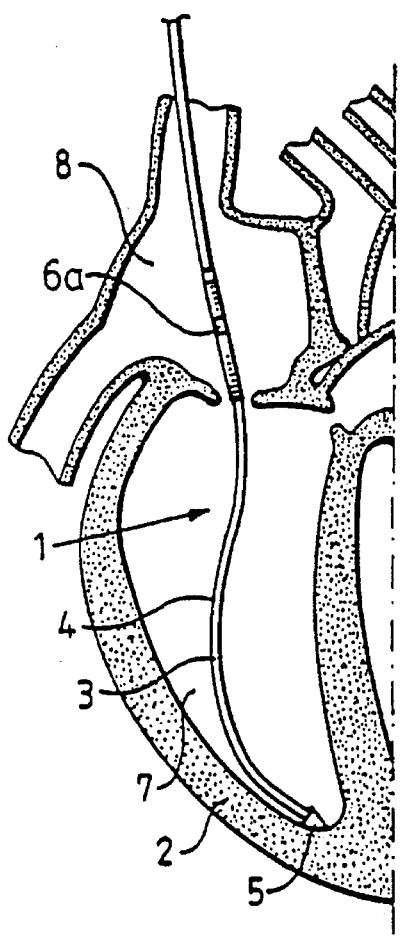
FIG. 1 is a section through a heart with an electrode apparatus according to the invention in the form of a pacemaker electrode apparatus applied therein.

FIG. 1 shows a bipolar pacemaker electrode apparatus 1 which is applied in a patient's heart 2. The electrode apparatus 1 includes an electrode cable 3 with a jacket of insulation 4 enclosing a flexible conductor (not shown) connected to a stimulation electrode 5 on the distal end of the electrode cable 3. The jacket of insulation 4 also encloses an additional conductor (not shown), electrically connected to a conductive surface on the electrode cable 3, forming a second, e.g. an indifferent or sensing, electrode 6a. In this embodiment, the electrode 5 is anchored in the ventricle 7, and the second electrode 6a is floatingly arranged in the atrium 8. This means that the electrode 6a is not attached to the heart wall. The distance between the electrodes 5 and 6a can be varied with the pacemaker electrode apparatus described herein, as will be described in conjunction with several of the FIGS. 3–12.

Figure 2:
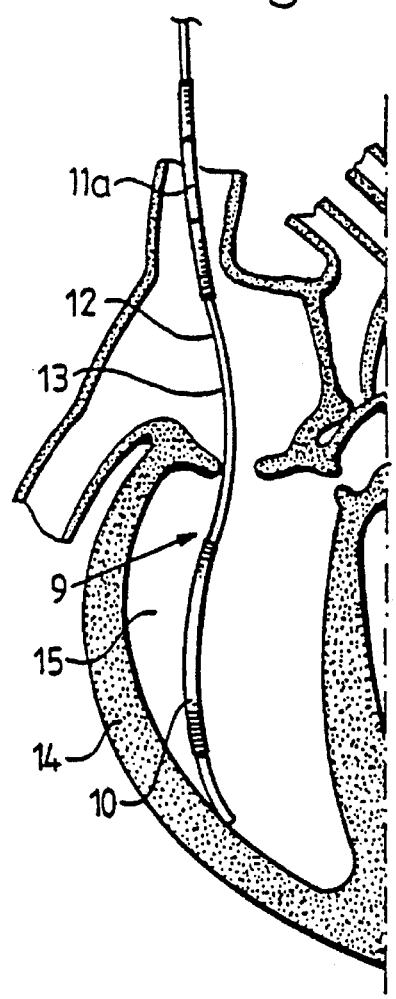
FIG. 2 is a section through a heart with a partially applied electrode apparatus according to the invention in the form of a defibrillation electrode apparatus.

FIG. 2 shows a defibrillation electrode apparatus 9, applied to a patient, consisting of an electrode cable 12 with a sleeve of insulation 13 enclosing two insulated conductors (not shown), one conductor of which is connected to a first defibrillation electrode 10 on the electrode cable 12 and the second conductor is connected to a conductive surface, a portion of which serves as a second defibrillation electrode 11a, on the electrode cable 12 spaced a distance from the defibrillation electrode 10. In this embodiment, the first defibrillation electrode 10 is located in the ventricle 15 of the heart 14, and the second defibrillation electrode 11a is arranged in the superior vena cava. The distance between the electrodes 10 and 11a for this defibrillation electrode apparatus 9 can be varied, as described in conjunction with several of the FIGS. 3–12.

Figure 3:
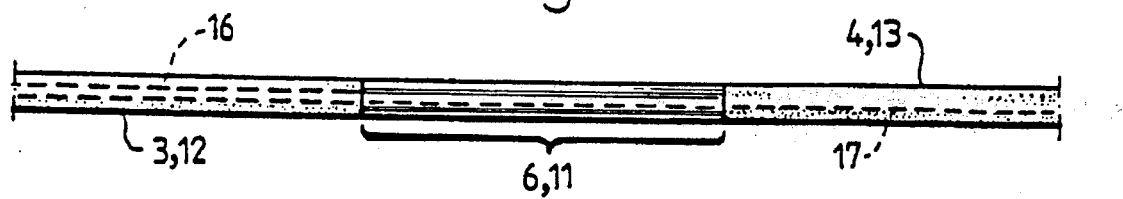
FIGS. 3–12 respectively show parts of the defibrillation and pacemaker apparatus which explain the invention in various embodiments.

FIG. 3 shows part of the electrode cable 3 or 12 for the pacemaker or defibrillation electrode apparatus 1 or 9 with a conductive surface 6 or 11 (used to form the electrode 6a or 11a) covering a desired part of the jacket of insulation 4 or 13. The conductive surface 6 or 11, which is connected to the aforementioned helical conductor 16 inside the jacket of insulation 4 or 13, is formed by a very thin coating of a conductive material deposited on the jacket of insulation 4 or 13 to enable the electrode cable 3 or 12 to retain its flexibility. The conductive surface 6 or 11 can alternatively be formed as a part of the helical conductor 16, which is stripped of the insulation jacket 4 or 13. The second conductor, connected to the first electrode 5 or 10, mentioned in conjunctions with FIGS. 1 and 2 is designated 17. In FIG. 3, the conductors 16 and 17 are shown in stylized form with dashed lines.

Figure 4:
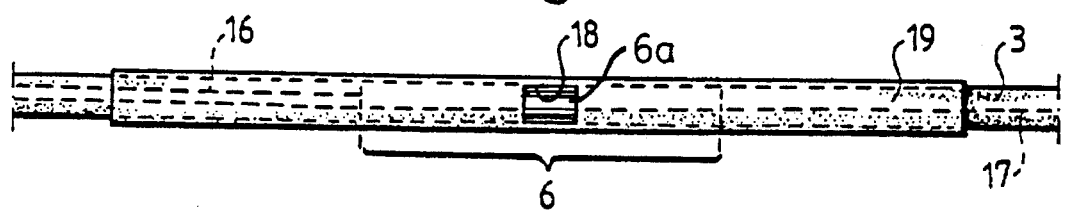

FIG. 4 shows a sleeve-like body 19, made from an insulating material having a window-like opening 18, which can be slid along the electrode cable 3. The body 19 is arranged on the electrode cable 3 in such a way that it covers the conductive surface 6. Only the window 18 exposes part of this surface 6, this exposed part forming the electrode 6a. When the body 19 is slid along the electrode cable 3, the window 18 is also displaced, and accordingly, the location of the portion of the conductive surface 6 forming the second electrode 6a (in a bipolar pacemaker apparatus 1 in this embodiment) is selectable. The distance between the electrode 5 and electrode 6 is also varied by the described displacement of the window 18. The length of the body 19 is preferably such that the body 19 covers (i.e., is coextensive with or extends beyond) the conductive surface 6 even when the window 18 has been moved to a position in which some peripheral part of the surface 6 forms the electrode 6a.

Figure 5:
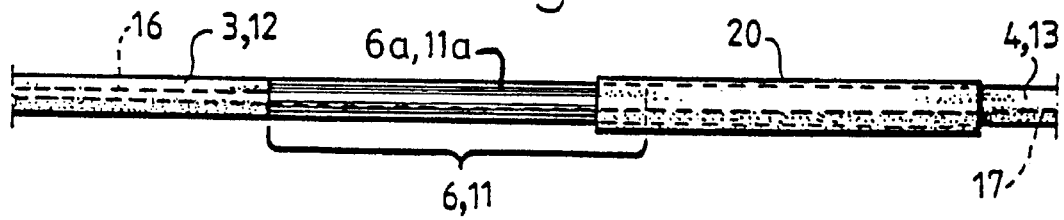

In the embodiment of FIG. 5 the electrode cable 3 or 12 for a pacemaker or defibrillation electrode apparatus 1 or 9 is provided with a windowless, sleeve-like, flexible body 20. This embodiment shows that the body 20 can be moved in relation to the conductive surface 6 or 11 in such a way, that most of this surface 6 or 11 is exposed. The exposed part of the surface 6 or 11 can be enlarged or reduced in size (longitudinal extent) when the body 20 is slid in one direction or the other. There is a simultaneous change in the distance between the portion of the surface 6 or 11 which serving as the electrode 6a or 11a, and the first electrode 5 or 10.

Figure 6:
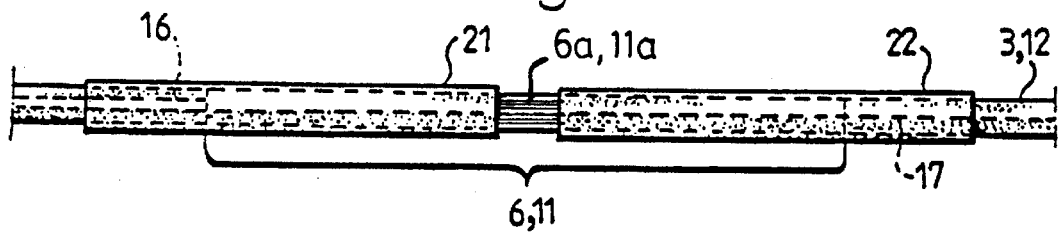

In the embodiment of FIG. 6, the electrode cable 3 or 12 is provided with two windowless, flexible bodies 21 or 22 which can be slid against each other along the electrode cable 3 or 12 and along the conductive surface 6 or 11 so a pacemaker or defibrillation electrode 6a or 11a whose size and position are adjustable, can be achieved. The exposed conductive surface always serves as the electrode 6a or 11a.

The shift of the bodies 19 and 22 described in conjunction with the embodiments of FIGS. 4–6 is always performed by the physician before the electrode apparatus 1 or 19 is implanted.

Figure 7:
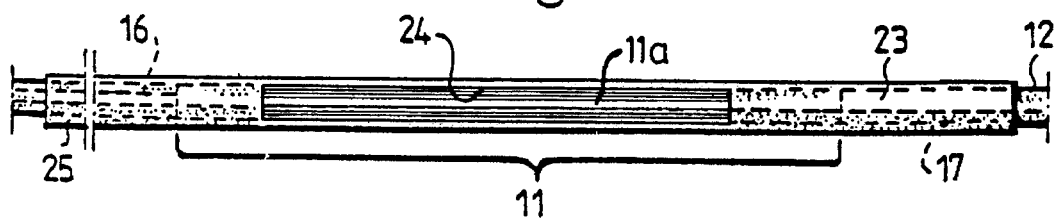

FIG. 7 shows another embodiment of a sleeve-like body 23 arranged on the electrode cable 12. The body 23 is equipped with an elongated window 24 which accordingly exposes the conductive surface 11, which is very large compared to the window 18 shown and described in conjunction with FIG. 4, serving as the defibrillation electrode 11a in this example. FIG. 7 also shows that the body 23 is long enough to make its proximal end 25 accessible to the physician, even after an electrode apparatus has been implanted. This accessibility can be very useful to the physician, since the window 24 can be rotated around the longitudinal axis of the cable 12, and the exposed portion 11a of the conductive surface 11 can be aimed in the desired direction, achieving a favorable distribution of current in the heart tissue. In this embodiment, the sleeve-like body 23 can also be slid along the electrode cable 12, thereby changing the distance between the electrodes 10 and 11a.

The extended-length body 23 described herein can be used in conjunction with several of the previously described embodiments, e.g. the body 19 described in FIG. 4 which could advantageously have the extended length.

Figure 8:
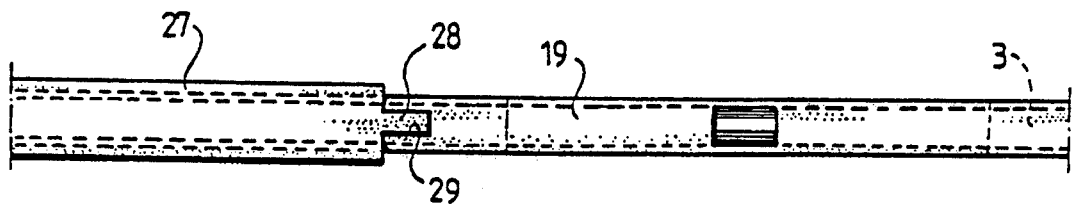

Another way to control a relatively short sleeve-like body, e.g. the body 19, with an implanted electrode apparatus is with a control element 27, shown in FIG. 8. The control element 27 is a tubular, flexible part which is temporarily connectable to the body 19, and which has a length such that the physician is able to grasp the proximal end of the control device 27 even after implantation. In the embodiment of FIG. 8, the distal end of the control element 27 is equipped with a projecting part 28 which can be inserted into a corresponding recess 29 in the body 19. Using this control element 27, the physician would then be able to slide the body 19 along the electrode cable 3 and rotate the body 19 around its longitudinal axis. The means for connecting the distal end of the control element 27 to the body 19 could be devised in ways other than the one shown in FIG. 8. If the physician does not wish to rotate the body 19 around its longitudinal axis but merely to slide it along the electrode cable 3, the control element 27 does not have to be equipped with any connecting means. The internal diameter of the tubular control element 27 is preferably somewhat larger than the external diameter of the electrode cable 3, thereby reducing friction between these parts.

Figure 9:
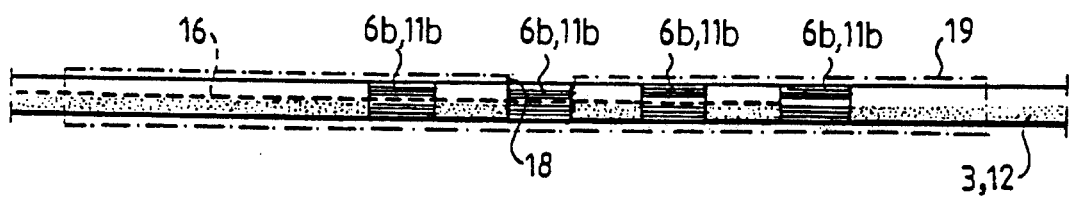

FIG. 9 shows that the conductive surface 6 or 11 can be formed by a number of successively spaced sub-surfaces 6b and 11b connected to a common conductor 16. An electrode cable 3 or 12 provided with such sub-surfaces can be advantageously used with a pacemaker electrode apparatus 1 in which e.g. the body 19 is slidable on the electrode cable 3 and in which the length of the window 18 roughly corresponds to the length of one sub-surface. In FIG. 9 the body 19 is designated with dashed lines. FIG. 9 also shows that the window 18 can be wider than has been shown for previous embodiments. Depending on the size of the sub-surfaces, an embodiment of the kind described here can also be used with a defibrillation electrode apparatus 9.

Figure 10:
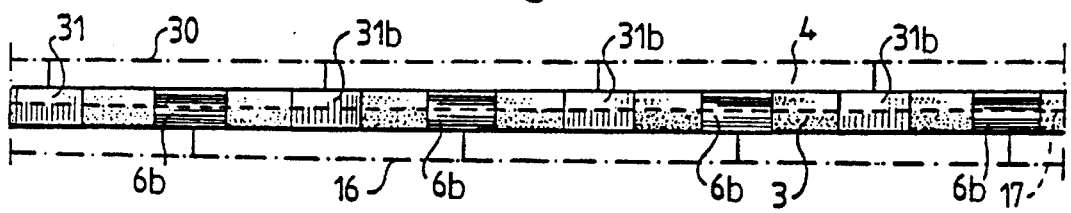
Figure 11:
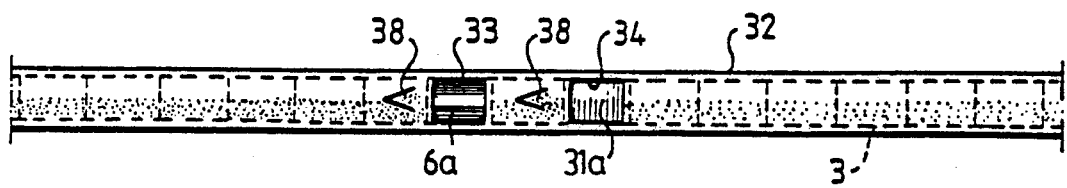

FIG. 10 shows a multipolar pacemaker electrode apparatus 1 in which the electrode cable 3 is equipped with a third conductor 30, arranged inside the jacket of insulation 4 and connected to a second conductive surface arranged on the electrode cable, in addition to the previously described conductors 16 and 17. The previously described first conductive surface and the second conductive surface are subdivided into sub-surfaces 6b and 31b separately spaced along the electrode cable 3. For clarity, the conductors 16 and 30 are schematically rendered with dashed lines outside the electrode cable 3 with a connection to the respective sub-surfaces 6b and 31b. This electrode cable 3 is preferably provided with a sleeve-like body 32 with two openings or windows 33 and 34, successively spaced at a distance corresponding to the distance between two adjacent sub-surfaces 6b and 31b. One such sleeve-like body 32 is shown in FIG. 11. To prevent one window 33 or 34 from simultaneously exposing parts of both a first and second sub-surface 6b and 31b, the length of each window 33 and 34 is less than the distance between the sub-surfaces 6b and 31b. When the body 32 is slid along the electrode cable 3, the distance between the first electrode 5 and the sub-surfaces 6b and 31b changes, thereby forming two additional electrodes 6a and 31a. FIG. 11 shows that the sleeve-like body 32 is equipped with projecting fixing means in the form of tines 38 arranged by the windows 33 and 34. Using the fixing means, the body 32 can be attached to the heart wall so the exposed portions 6a and 31 come into direct contact with excitable tissue, thereby resulting in a very low stimulation threshold.

Figure 12:
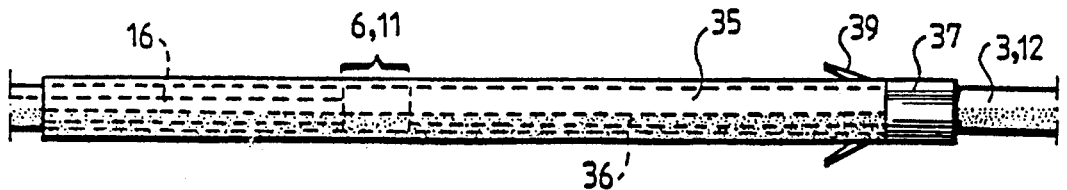

FIG. 12 shows a sleeve-like body 35 which has been slid onto the electrode cable 3 or 12 for the pacemaker or defibrillation electrode apparatus 1 or 9. The interior wall of the body 35 is provided with a conductive coating 36, e.g. in the form of a strip running along the entire length of the body 35, as shown in FIG. 12. The conductive coating 36 is connected to an electrode 37, arranged on top of the body 35, which forms the second electrode in one of the electrode apparatuses 1 or 9. In this embodiment, the electrode 37 is arranged on one end of the body 35. As a result of the strip-shaped conductive coating 36, the electrode 37 is always in connection with the first conductive surface 6 or 11 as long as the body 35 covers this surface 6 or 11 on the electrode cable 3 or 12. The electrode 37 can be arranged anywhere on top of the body and may even have a larger area than the one shown in this FIG. 12. The electrode surface does not necessarily have to be ring-shaped. A relatively large conductive surface on the body 35 can serve as a defibrillation electrode. When the body 35 is slid along the electrode cable 3 or 12, the distance between this electrode and the first electrode 5 or 10 can be enlarged or reduced. An electrode which is not ring-shaped can be aimed in the desired direction if the body 35 is rotated around its longitudinal axis. The body 35 also has tines 39 which are arranged next to the electrode 37.

Figure 13:
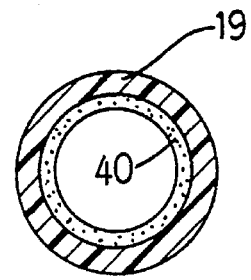
FIGS. 13 and 14 show embodiments for applying lubricant between the sleeve body and the electrode surface of the cable.
Figure 14:
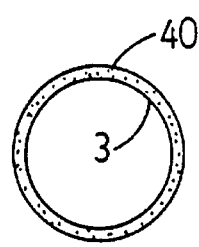

In order to facilitate sliding or rotation of the sleeve-like bodies 19–23, 32 and 35, their interior walls (FIG. 13) and/or the surface of the electrode cable 3 or 12 on which the bodies slide (FIG. 14) can be provided with a coating of lubricant 40.

Within the scope of the invention the first electrode 5 for the pacemaker electrode apparatus 1 and the electrode 10 for the defibrillation electrode apparatus can be constructed in the way described herein for the second electrode/second electrodes. The invention achieves an electrode apparatus wherein one or a number of electrodes can be continually slid along the electrode cable so these electrodes can be placed in the desired position in the patient. The size and aiming of the electrode can also be varied in some instances.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical electrode system comprising:

a flexible, longitudinally extending cable adapted for implantation in a medical subject and having an exterior insulating jacket containing first and second flexible electrical conductors;

an exposed, first electrode carried on said cable and electrically connected to said first electrical conductor;

said cable having an electrically conductive surface electrically connected to said second electrical conductor and disposed a distance from said first electrode and exposed to the exterior of said cable;

a sleeve body surrounding said cable and extending over a longitudinal portion of said cable, said sleeve body being selectively positionable on said cable to partially cover said electrically conductive surface and to leave a remainder of said electrically conductive surface exposed at a selected position relative to said first electrode, said remainder of said conductive surface forming a second electrode; and a control element temporarily engage able with said sleeve body for selectively positioning said sleeve body on said cable to select the position of said exposed surface relative to said first electrode.

2. A medical electrode system as claimed in claim 1 wherein said sleeve body comprises a solid-walled tube having opposite ends, and wherein said remainder of said electrically conductive surface comprises a portion of said electrically conductive surface disposed adjacent one of said ends of said tube.

3. A medical electrode system as claimed in claim 1 wherein said sleeve body comprises a tube having a tube wall with at least one opening therein, said opening exposing said remainder of said electrically conductive surface, and said opening having a longitudinal extent which is less than a longitudinal extent of said electrically conductive surface, and said tube being rotatable around said cable.

4. A medical electrode system as claimed in claim 3 wherein said control element temporarily engageable with said end of said sleeve body comprises means for controlling rotation of said sleeve body around said cable.

5. A medical electrode system as claimed in claim 4 wherein said control element temporarily engageable with said end of said sleeve body further comprises means for controlling sliding of said sleeve body longitudinally along said cable.

6. A medical electrode system as claimed in claim 1 wherein said electrically conductive surface comprises a thin electrically conductive coating deposited on the exterior of said insulating jacket.

7. A medical electrode system as claimed in claim 1 wherein said electrically conductive surface comprises a portion of said second conductor exposed by removal of said insulating jacket in registry with said portion of said second electrical conductor.

8. A medical electrode system as claimed in claim 1 wherein said electrically conductive surface comprises at least two spaced-apart sub-surfaces.

9. A medical electrode system as claimed in claim 1 further comprising an additional sleeve body also surrounding said cable and extending over a longitudinal portion of said cable, said additional sleeve body being disposed on said cable to partially cover said electrically conductive surface and, in combination with said sleeve body, to leave a remainder of said electrically conductive surface exposed at said selected position relative to said first electrode.

10. A medical electrode system as claimed in claim 1 wherein said electrode cable comprises a third flexible electrical conductor contained in said insulating jacket and a second electrically conductive surface, electrically connected to said third electrical conductor and disposed a distance from said first electrode and exposed to the exterior of said cable, said first and second electrically conductive surfaces each being divided into a plurality of sub-surfaces longitudinally spaced from each other along said electrode cable, and wherein said sleeve body simultaneously exposes at least one sub-surface of each of said first and second conductive surfaces.

11. A medical electrode system as claimed in claim 10 wherein said sleeve body comprises a tube with a tube wall having two openings therein, said openings being spaced from each other by a distance corresponding to a spacing between two adjacent ones of said sub-surfaces of said first and second conductive surfaces, and wherein each of said openings has a longitudinal extent which is less than said distance.

12. A medical electrode system as claimed in claim 1 wherein said control element temporarily engageable with said end of said sleeve body comprises means for controlling sliding of said sleeve body longitudinally along said cable.

13. A medical electrode system as claimed in claim 1 further comprising fixing elements projecting from said sleeve body adapted for interacting with tissue of said medical subject to hold said cable in place within said medical subject.

14. A medical electrode system as claimed in claim 13 wherein said sleeve body comprises a tube having a tube wall with at least one opening therein which exposes said remainder of said electrically conductive surface at said selected position, and wherein said fixing elements are disposed adjacent said at least one opening.

15. A medical electrode system as claimed in claim 1 further comprising a coating of lubricant on said exterior insulating jacket of said cable.

16. A medical electrode system as claimed in claim 1 wherein said sleeve body has an interior wall, and further comprising a lubricant coating said interior wall of said sleeve body.

17. A medical electrode system comprising:
a flexible, longitudinally extending cable adapted for implantation in a medical subject and having an exterior insulating jacket containing first and second flexible electrical conductors;
an exposed first electrode carried on said cable and electrically connected to said first electrical conductor;
said cable having an electrically conductive surface electrically connected to said second electrical conductor and disposed a distance from said first electrode and exposed to the exterior of said cable;
a sleeve body surrounding said cable and extending over a longitudinal portion of said cable, said sleeve body being selectively positionable on said cable to provide a current path between said electrically conductive surface and said medical subject, said current path including a second electrode and said second electrode having a position relative to said first electrode which is selectively variable by displacing said sleeve body relative to said cable: and
a control element temporarily engageable with said sleeve body for selectively positioning said sleeve body on said cable to select the position of said exposed surface relative to said first electrode.

18. A medical electrode system as claimed in claim 17 wherein said sleeve body comprises a solid-walled tube having opposite ends, and wherein said second electrode comprises a portion of said electrically conductive surface disposed adjacent one of said ends of said tube.

19. A medical electrode system as claimed in claim 17 wherein said sleeve body comprises a tube having a tube wall with at least one opening therein, said opening exposing said second electrode, and said opening having a longitudinal extent which is less than a longitudinal extent of said electrically conductive surface, and said tube being rotatable around said cable.

20. A medical system apparatus as claimed in claim 17 further comprising an additional sleeve body also surrounding said cable and extending over a longitudinal portion of said cable, said additional sleeve body being disposed on said cable to partially cover said electrically conductive surface and, in combination with said sleeve body, to leave a remainder of said electrically conductive surface exposed at a selected position relative to said first electrode.

21. A medical electrode system as claimed in claim 17 wherein said sleeve body has an interior wall with a conductive coating on said interior wall, and said sleeve body carrying said second electrode at an exterior of said sleeve body and electrically connected to said conductive coating, said conductive coating being in electrical contact with said electrically conductive surface on said cable.

22. A medical electrode system as claimed in claim 21 wherein said sleeve body has an end, and wherein said electrode on said sleeve body forming said second electrode is disposed at said end of said sleeve body.

23. A medical electrode system as claimed in claim 17 wherein said electrically conductive surface comprises a thin electrically conductive coating deposited on the exterior of said insulating jacket.

24. A medical electrode system as claimed in claim 17 wherein said electrically conductive surface comprises a portion of said second conductor exposed by removal of said insulating jacket in registry with said portion of said second electrical conductor.

25. A medical electrode system as claimed in claim 17 wherein said electrically conductive surface comprises at least two spaced-apart sub-surfaces.

26. A medical electrode system as claimed in claim 17 wherein said electrode cable comprises a third flexible electrical conductor contained in said insulating jacket and a second electrically conductive surface, electrically connected to said third electrical conductor and disposed a distance from said first electrode and exposed to the exterior of said cable, said first and second electrically conductive surfaces each being divided into a plurality of sub-surfaces longitudinally spaced from each other along said electrode cable, and wherein said sleeve body simultaneously exposes at least one sub-surface of each of said first and second conductive surfaces.

27. A medical electrode system as claimed in claim 17 wherein said sleeve body comprises a tube with a tube wall having two openings therein, said openings being spaced from each other by a distance corresponding to a spacing between two adjacent ones of said sub-surfaces of said first and second conductive surfaces, and wherein each of said openings has a longitudinal extent which is less than said distance.

28. A medical electrode system as claimed in claim 27 wherein said control element temporarily engageable with said end of said sleeve body comprises means for controlling rotation of said sleeve body around said cable.

29. A medical electrode system as claimed in claim 27 wherein said control element temporarily engageable with said end of said sleeve body comprises means for controlling sliding of said sleeve body longitudinally along said cable.

30. A medical electrode system as claimed in claim 17 further comprising fixing elements projecting from said sleeve body adapted for interacting with tissue of said medical subject to hold said cable in place within said medical subject.

31. A medical electrode system as claimed in claim 30 wherein said sleeve body comprises a tube having a tube wall with at least one opening therein which exposes said remainder of said electrically conductive surface at said selected position, and wherein said fixing elements are disposed adjacent said at least one opening.

32. A medical electrode system as claimed in claim 31 wherein said control element temporarily engageable with said end of said sleeve body comprises means for controlling rotation of said sleeve body around said cable.

33. A medical electrode system as claimed in claim 32 wherein said control element temporarily engageable with said end of said sleeve body further comprises means for controlling sliding of said sleeve body longitudinally along said cable.

34. A medical electrode system as claimed in claim 17 further comprising a coating of lubricant on said exterior insulating jacket of said cable.

35. A medical electrode system as claimed in claim 17 wherein said sleeve body has an interior wall, and further comprising a lubricant coating said interior wall of said sleeve body.

36. A medical electrode system as claimed in claim 17 wherein said control element temporarily engageable with said end of said sleeve body further comprises means for controlling sliding of said sleeve body longitudinally along said cable.

* * * * *